United States Patent [19]

Appleton et al.

[11] Patent Number: 4,810,719
[45] Date of Patent: Mar. 7, 1989

[54] ANTI-INFLAMMATOR 1,N-DIARYLPYRAZOL-3-AMINES

[75] Inventors: Richard A. Appleton, Melton Mowbray; Sidney C. Burford; David N. Hardern, both of Loughborough, all of England; David Wilkinson, Shepshed, United Kingdom

[73] Assignee: Fisons plc, Ipswich, England

[21] Appl. No.: 733,591

[22] Filed: May 10, 1985

[30] Foreign Application Priority Data

May 12, 1984 [GB] United Kingdom ............... 8412181
Nov. 17, 1984 [GB] United Kingdom ............... 8429128

[51] Int. Cl.$^4$ ........................................... A61K 31/415
[52] U.S. Cl. ................................ 514/406; 544/328; 546/159; 546/279; 548/162; 548/190; 548/362; 548/374; 548/375; 548/376; 514/275; 514/313; 514/341; 514/367; 514/370
[58] Field of Search ................ 548/362, 375, 376; 514/406

[56] References Cited

U.S. PATENT DOCUMENTS

| 4,149,005 | 4/1979 | Battisti et al. ............ 548/362 |
| 4,434,292 | 2/1984 | Heinemann et al. ............ 548/379 |
| 4,564,684 | 1/1986 | Copp et al. ............ 548/379 |

FOREIGN PATENT DOCUMENTS

| 149231 | 7/1981 | German Democratic Rep. ............ 548/376 |
| 151366 | 10/1981 | German Democratic Rep. ............ 548/376 |
| 743505 | 1/1956 | United Kingdom ............ 548/362 |
| 1100754 | 1/1968 | United Kingdom ............ 548/362 |

OTHER PUBLICATIONS

Scherowsky et al., Chem. Ber. 116, 186-196(1983).

Primary Examiner—Mary C. Lee
Assistant Examiner—Mary Sue Howard
Attorney, Agent, or Firm—Marshall, O'Toole, Gerstein, Murray & Bicknell

[57] ABSTRACT

There are described compounds of formula I,

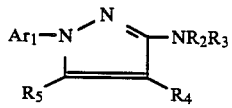

in which
either $R_2$ represents hydrogen, alkyl or $Ar_2$, and
$R_3$ represents hydrogen, alkyl or alkyl substituted by $Ar_3$;
or $R_2$ and $R_3$ together form the chain $-(CH_2)_m-$;
$R_4$ and $R_5$, which may be the same or different, each independently represent hydrogen, halogen, Ar, alkyl, or alkyl substituted by Ar,
$Ar_1$, $Ar_2$ and Ar, which may be the same or different each independently represent aryl or aryl substituted by one or more of
halogen, hydroxy, $-CN$, $-COR_6$, trihalomethyl, alkoxy, alkoxy substituted by $-COR_6$, alkoxy substituted by $-NR_7R_8$, alkyl, alkyl substituted by $-COR_6$, alkyl substituted by $NR_7R_8$, alkoxy substituted by $Ar_3$, $S(O)_nR_9$, $-NR_7R_8$ or $OAr_3$;
$R_6$ represents $-OR_{10}$, $-NR_7R_8$, hydrogen or alkyl;
$R_7$ and $R_8$, which may be the same or different, each independently represent hydrogen, alkyl, alkanoyl or $Ar_3$;
$R_9$ represents alkyl or $Ar_3$;
$R_{10}$ represents hydrogen, alkyl or $Ar_3$;
m represents an integer from 3 to 6 inclusive;
n represents 0, 1 or 2; and
$Ar_3$ represents unsubstituted aryl;
or a pharmaceutically acceptable derivative thereof.

There are also described compositions containing the compounds and methods for their preparation.

The compounds are indicated for use as pharmaceutical, e.g. anti-inflammatory, agents.

5 Claims, No Drawings

ANTI-INFLAMMATOR 1,N-DIARYLPYRAZOL-3-AMINES

This invention relates to new heterocyclic compounds, processes for their preparation and compositions containing them.

High molecular weight polymer formulations containing certain substituted 1,5,N-triphenylpyrazol-3-amines are disclosed in East German Patent No 149231. Dyestuffs with improved light stability and containing similar 1,5,N-triphenylpyrazol-3-amines are described in East German Patent No 151366. Neither of these patents discloses any pharmacological activity for these compounds.

We have now found that certain 1,N-diarylpyrazol-3-amines have useful pharmacological properties.

According to the invention there is provided a compound of formula I,

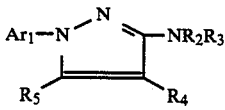

in which
either $R_2$ represents hydrogen, alkyl or $Ar_2$, and
$R_3$ represents hydrogen, alkyl or alkyl substituted by $Ar_3$;
or $R_2$ and $R_3$ together form the chain $-(CH_2)_m-$;
$R_4$ and $R_5$, which may be the same or different, each independently represent hydrogen, halogen, Ar, alkyl, or alkyl substituted by Ar,
$Ar_1$, $Ar_2$ and Ar, which may be the same or different each independently represent aryl or aryl substituted by one or more of
halogen, hydroxy, $-CN$, $-COR_6$, trihalomethyl, alkoxy, alkoxy substituted by $-COR_6$, alkoxy substituted by $-NR_7R_8$, alkyl, alkyl substituted by $-COR_6$, alkyl substituted by $NR_7R_8$, alkoxy substituted by $Ar_3$, $S(O)_nR_9$, $-NR_7R_8$ or $OAr_3$;
$R_6$ represents $-OR_{10}$, $-NR_7R_8$, hydrogen or alkyl;
$R_7$ and $R_8$, which may be the same or different, each independently represent hydrogen, alkyl, alkanoyl or $Ar_3$;
$R_9$ represents alkyl or $Ar_3$;
$R_{10}$ represents hydrogen, alkyl or $Ar_3$;
m represents an integer from 3 to 6 inclusive;
n represents 0, 1 or 2; and
$Ar_3$ represents unsubstituted aryl; or a pharmaceutically acceptable derivative thereof,
for use as a pharmaceutical.

According to the invention, there are also provided the compounds of formula I, as defined above, provided that
(i) $R_2$ and $R_3$ do not both represent hydrogen;
(ii) when $R_3$ and $R_4$ represent hydrogen and $R_5$ and $R_2$ both represent phenyl, then $Ar_1$ does not represent phenyl, 4-methylphenyl or 4-methoxyphenyl;
(iii) when $R_3$ and $R_4$ both represent hydrogen, $R_5$ represents phenyl and $R_2$ represents 4-methylphenyl, then $Ar_1$ does not represent phenyl or 4-bromophenyl;
(iv) when $R_3$ and $R_4$ both represent hydrogen, $R_5$ represents 4-methoxyphenyl and $R_2$ represents 4-chlorophenyl, then $Ar_1$ does not represent phenyl; and
(v) when $R_3$ and $R_4$ both represent hydrogen, $R_5$ represents 4-methylphenyl and $R_2$ represents 4-hydroxyphenyl, then $Ar_1$ does not represent phenyl,
and pharmaceutically acceptable derivatives thereof.

According to the invention there is further provided a process for the preparation of compounds of formula I, or a pharmaceutically acceptable derivative thereof, which comprises
(a) selectively oxidising a corresponding compound of formula II,

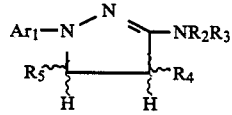

in which $Ar_1$, $R_2$, $R_3$, $R_4$ and $R_5$ are as defined above,
(b) producing a compound of formula I in which one or more of $Ar_1$, $Ar_2$ and Ar is substituted by OH, by hydrogenolysing a corresponding compound of formula I, in which one or more of $Ar_1$, $Ar_2$ and Ar is substituted by $OR_{20}$, in which $R_{20}$ is a hydrogenolysable group,
(c) producing a compound of formula I, in which one or more of $Ar_1$, $Ar_2$ and Ar is substituted by alkoxy, alkoxy substituted by $-COR_6$, alkoxy substituted by $-NR_7R_8$ or alkoxy substituted by $Ar_3$, by alkylating a corresponding compound of formula I in which one or more of $Ar_1$, $Ar_2$ and Ar is substituted by OH, with the appropriately substituted alkyl acting agent,
(d) producing a compound of formula I, in which one or more of $Ar_1$, $Ar_2$ and Ar is substituted by one or more of $-COOH$, alkoxy substituted by $-COOH$, or alkyl substituted by $-COOH$, by hydrolysing a corresponding compound of formula I in which one or more of $Ar_1$, $Ar_2$ and Ar is substituted by one or more of $-COOalkyl$, alkoxy substituted by $-COOalkyl$, or alkyl substituted by $-COOalkyl$,
(e) producing a compound of formula I, in which one or more of $Ar_1$, $Ar_2$ and Ar is substituted by $-OH$, by cleavage of a corresponding compound of formula I in which one or more of $Ar_1$, $Ar_2$ and Ar is substituted by $-Oalkyl$,
(f) producing a compound of formula I, in which one or more of $Ar_1$, $Ar_2$ and Ar is substituted by alkyl substituted by $NR_7R_8$, by reducing a corresponding compound of formula I in which one or more of $Ar_1$, $Ar_2$ and Ar is substituted by alkyl substituted by $-CONR_7R_8$,
(g) producing a compound of formula I, in which one or more of $Ar_1$, $Ar_2$ and Ar is substituted by $-COalkyl$ ortho to a $-OH$ group, by Fries rearrangement of a corresponding compound of formula I in which one or more of $Ar_1$, $Ar_2$ and Ar is substituted by $-O-COalkyl$,
(h) producing a compound of formula I, in which n is 1 or 2, by selectively oxidising a corresponding compound of formula I in which n is 0 or 1,
(i) producing a compound of formula I in which $Ar_2$ represents 4-hydroxy-2-thiazolyl, by reacting a corresponding compound of formula I, in which $R_2$ represents $-CSNH_2$ with alkyl 2-haloethanoate,
(j) producing a compound of formula I in which $R_5$ represents halogen, by reacting a corresponding compound of formula III,

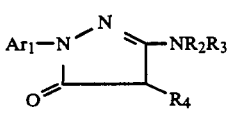

in which $Ar_1$, $R_2$, $R_3$ and $R_4$ are as defined above, with a halogenating agent, (k) producing a compound of formula I, in which $R_5$ represents hydrogen, by reducing a corresponding compound of formula I in which $R_5$ represents halogen, (l) reacting a compound of formula IV,

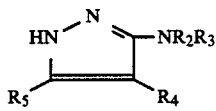

in which $R_2$, $R_3$, $R_4$ and $R_5$ are as described above, with a compound of formula V, $(Ar_1)_2ICl$  V in which $Ar_1$ is as defined above, or (m) producing a compound of formula I, containing a —COOalkyl group, by esterifying a corresponding compound of formula I containing a —COOH group, and where desired or necessary converting the compound of formula I to a pharmaceutically acceptable derivative thereof or vice versa.

In process (a), oxidising agents that may be used to convert a compound of formula II to a corresponding compound of formula I include metal catalysts, organic and inorganic oxidising agents, hypohalites and peroxides. Preferred metal catalysts include palladium on charcoal in the presence or absence of air. Preferred inorganic oxidising agents include manganese dioxide and chromium trioxide. Suitable organic oxidising agents include peracids, e.g. 3-chloroperbenzoic acid, and easily reduced hydrogen acceptors, e.g. 2,3-dichloro-5,6-dicyano-1,4-benzoquinone (DDQ). Hypohalite oxidants include aqueous hypochlorite, e.g. sodium hypochlorite (bleach) and organic hypohalites such as tertiary butyl hypochlorite. The oxidation may be carried out in a solvent which is inert to the reaction conditions. The choice of solvent depends on the compound to be oxidised and on the oxidising agent. However suitable solvents include halogenated hydrocarbons such as dichloromethane, alcohols, e.g. ethanol and aromatic hydrocarbons, e.g. toluene. The reaction may be carried out at a temperature of from about 0° to 150° C.

The compounds of formula II may be prepared by reacting a corresponding compound of formula VI,

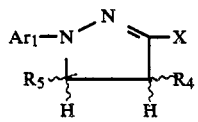

in which $Ar_1$, $R_4$ and $R_5$ are as defined above, and X is a good leaving group,
with a compound of formula VII, $R_3R_2NH$  VII in which $R_2$ and $R_3$ are as defined as above.

Good leaving groups that X may represent include halogen, e.g. chlorine or bromine, arylsulphonyl, hydroxy and esters thereof, alkoxy, e.g. methoxy or ethoxy, dihalophosphonyl, e.g. dichloro- or dibromophosphonyl, and —$NR_{11}R_{12}$, where $R_{11}$ and $R_{12}$ may each independently represent hydrogen or alkyl C1 to 6.

The compounds of formula VI may, in certain cases, exist in tautomeric forms. For example, when X represents hydroxy, the compound of formula II may exist as a mixture of tautomers of formula A and formula B,

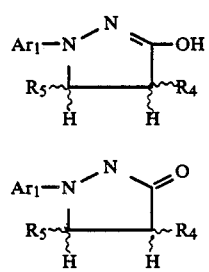

The reaction may be carried out with or without a solvent. When the reaction is carried out using a solvent, the solvent is preferably inert to the conditions of the reaction, for example a polar solvent such as 1,4-dioxan, ethanol, acetic acid, acetonitrile or dimethylformamide. However apolar solvents, e.g. toluene, may also be used. The reaction is preferably carried out at a temperature of from about 25° to 200° C.

The hydrogenolysis of process (b) may be carried out in a solvent which is inert to the reaction condition, e.g. in an alcoholic solvent such as ethanol. Hydrogenolysable groups that $R_{20}$ may represent include arylmethyl groups, in particular substituted and unsubstituted phenyl methyl groups. The reaction is preferably carried out using hydrogen at a pressure of from about 1 to 3 atmospheres using a metal catalyst or a support, e.g. palladium on charcoal. The hydrogenolysis is preferably carried out at a temperature of from about 0° to 50° C.

In process (c), the alkylation may be carried in a solvent, preferably a polar, aprotic solvent, e.g. dimethylformamide, 1,4-dioxan, acetonitrile or N-methyl pyrrolidone. Suitable alkylating agents include alkyl tosylates, diazoalkanes and alkyl halides, e.g. elkyl chlorides, bromides and iodides. When the aalkylating agent is an alkyl halide, the reaction is preferably carried out in the presence of a base, e.g. potassium carbonate, at a temperature of from about 0° to 100° C.

In process (d), the hydrolysis may be carried out under acidic or basic conditions. Suitable acidic conditions include hydrobromic acid in acetic acid. Suitable basic conditions include a strongly basic hydroxide, for example sodium hydroxide, in aqueous ethanol or methanol. The reaction may be carried out at a temperature of from about 0° to 120° C.

The hydrolysis of process (e) may be carried out under acidic conditions, e.g. using hydrobromic acid in acetic acid. The reaction is preferably carried out at a temperature of about 75° to 150° C.

The reduction of process (f) may be carried out using an electrophilic or nucleophilic reducing agent. Nucleophilic reducing agents include hydride reducing agents, e.g. lithium aluminium hydride. Electrophilic reducing agents include diborane. The reaction is preferably carried out in a solvent which is inert to the reaction conditions, e.g. diethyl ether, tetrahydrofuran or dioxan.

The Fries rearrangement of process (g) is preferably carried out in the presence of a Lewis acid such as zinc chloride, aluminium trichloride or boron trifluoride. The reaction may be carried out without a solvent or in the presence of a solvent which is inert to the reaction conditions, e.g. nitrobenzene. The reaction is preferably carried out at a temperature of from about 100° to 200° C.

The oxidation of process (h) is preferably carried out in a solvent which is inert to the reaction conditions, e.g. a halogenated hydrocarbon such as dichloromethane or dichloroethane. Suitable oxidising agents include organic peracids, in particular, 3-chloroperbenzoic acid. The degree of oxidation may be controlled by varying the proportion of oxidant used. The reaction may be carried out at a temperature of 0° to 75° C., e.g. room temperature.

The reaction of process (i) is preferably carried out in a solvent, for example a polar solvent such as ethanol. The reaction may be carried out at a temperature of from about 0° to 100° C., e.g. at the reflux temperature of the solvent. Preferred alkyl 2-haloethanoate include alkyl C1 to 6 esters, e.g. ethyl or methyl. Preferred halogens include chlorine and bromine.

The halogenation of process (j) may be carried out in the presence or absence of a solvent. Preferably the reaction is carried out using an excess of the halogenating agent as solvent and removing the excess by distillation when the reaction is complete. When the halogen is chloride, suitable chlorinating agents include thionyl chloride and phosphorus oxychloride. When the halogen is bromide or iodide, the corresponding phosphorus trihalide may be used.

The reduction of process (k) may be carried out under conditions analogous to those described under process (b).

The arylation of process (1) is preferably carried out in the presence of a non-nucleophilic base, e.g. sodium hydride. The reaction is preferably carried out in a polar, aprotic solvent, e.g. dimethylformamide or 1,4-dioxan, at a temperature of from about 0° to 100° C., e.g. room temperature.

The esterification of process (m) may be carried out under acid catalysed conditions, using the required alkyl alcohol in excess of the alcohol as solvent. Alternatively, the reaction may be effected, particularly for alkyl C1 to 6, by reacting the corresponding carboxylic acid with the appropriate diazoalkyl compound in an aprotic solvent, e.g. ether or dichloromethane.

The pyrazole starting materials of processes (b), (c), (d), (e), (f), (g), (h), (1) and (m) may be made by processes analogous to those described in process (a). The pyrazole starting material for process (k) may be made by a process analogous to process (j).

The compounds of formulae III, IV, V, VI and VII are either known, or may be made from known compounds using conventional techniques known per se.

The acid addition salts of the compounds of formula I may be prepared by reaction of the free base with an appropriate acid. The acid addition salts may be converted to the corresponding free base by the action of a stronger base.

The processes as described above may produce the compound of formula I or a derivative thereof. It is also within the scope of this invention to treat any derivative so produced to liberate the free compound of formula I, or to convert one derivative into another.

The compounds of formula I and the intermediates therefore may be isolated from their reaction mixtures using conventional techniques.

Pharmaceutically acceptable derivatives of the compounds of formula I include pharmaceutically acceptable acid addition salts. Suitable salts include salts of mineral acids, for example, hydrohalic acids, e.g. hydrochloric acid or hydrobromic acid, or organic acids, e.g. formic, acetic or lactic acids. The acid may be polybasic, for example sulphuric, fumaric or citric acid.

When the compound of formula I includes a group $-COR_6$, in which $R_6$ represents hydroxy, pharmaceutically acceptable derivatives include pharmaceutically acceptable salts, esters and amides. Suitable salts include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl) methylamine, with simple monocyclic nitrogen heterocyclic compounds, e.g. piperidine or morpholine, with an amino acid, e.g. lysine, ornithine, arginine, or an N-alkyl, especially an N-methyl derivative of any one thereof, or with an aminosugar, e.g. glucamine, N-methylglucamine or glucosamine. Suitable esters include simple lower alkyl esters, e.g. the ethyl ester, esters derived from alcohols containing basic groups, e.g. bis-lower alkylamino substituted alkanols such as the 2-(diethylamino)-ethyl ester, and acyloxy alkyl esters, e.g. a lower acyloxy-lower alkyl ester such as the pivaloyloxymethyl ester. The pharmaceutically acceptable acid addition salts of the basic esters, e.g. the hydrochloride, the hydrobromide, the maleate or the fumarate salts, may also be used. The esters may be made by conventional techniques, e.g. esterification or transesterification. The amides may be, for example, unsubstituted or mono- or di- C1 to 6 alkyl or phenyl amides and may be made by conventional techniques, e.g. reaction of an ester of the corresponding acid with ammonia or an appropriate amine.

Other pharmaceutically acceptable derivatives are compounds which will be suitable bioprecursors (prodrugs) of the compounds of formula I and will be readily apparent to those skilled in the art and may be made from the compounds of formula I using conventional processes known per se or by processes analogous to those described above.

The compounds of formula I, and pharmaceutically acceptable derivatives thereof, are useful because they possess pharmacological activity in animals. In particular, the compounds are useful as broad spectrum anti-inflammatory agents as indicated in one or more of the following assay systems:

(a) Inhibition of lipoxygenases, e.g. 5, 12 and 15 lipoxygenase, in the presence of exogenous arachidonic acid and measurement of the enzyme activity by either a modification of B A Jakschik et al, Biochemical and Biophysical Research Communications, 95(1), 103, (1980) using reverse phase HPLC to quantify the products or by a modification of the method of F F Sun et al, Prostaglandins 21 (2) 333 (1981) using uv absorption to quantify product formation.

(b) Inhibition of prostaglandin synthetase, utilising bovine seminal vesicle microsomes as the enzyme source after the method of Egan et al Biochemistry 17, 2230 (1978) using either radiolabelled arachidonic acid as substrate and product separation by thin layer chromatography and quantification by scintillation counting or unlabelled arachidonic acid as substrate and a specific radioimmunoassay kit (New England Nuclear) to measure prostaglandin $E_2$ produced.

(c) Inhibition of 5 lipoxygenase activity in intact huma neutrophils stimulated by ionophore A23187 and supplemented with exogenous arachidonic acid after the method of P Borgeat and B Samuelsson, Proceedings New York Academy of Science 70 2148 (1979) using reverse phase HPLC to measure the products.

(d) Inhibition of formation of arachidonic acid metabolites by mouse peritoneal macrophages challenged in vitro with immune complexes by the method of Blackham et al, J. Pharm. Pharmac. (1985).

(e) Inhibition of $PGE_2$ formation and cell infiltration in the carrageenin sponge model by the method of Higgs et al, Eur. J. Pharmac. 66 81 (1980).

(f) Inhibition of immune complex mediated inflammation in the mouse peritoneal cavity by the method of Blackham et al, J. Pharmac. Methods (1985).

(g) Inhibition of carrageenin oedema in the rat by the method of Winter et al, Proc. Soc. Exp. Biol. 111 544 (1962).

(h) Inhibition of bronchial anaphylaxis in guinea pigs by the method of Anderson, Br. J. Pharmac. 77 301 (1982).

The compounds are indicated for use in the treatment or prophylaxis of inflammatory conditions in mammals, including man. Conditions that may be specifically mentioned are: rheumatoid arthritis, rheumatoid spondylitis, osteoarthritis, gouty arthritis, and other arthritic conditions, inflamed joints;

eczema, psoriasis or other inflammatory skin conditions such as sunburn;

inflammatory eye conditions including conjunctivitis;

lung disorders in which inflammation is involved, e.g. asthma, bronchitis, pigeon fancier's disease and farmer's lung;

conditions of the gastrointestinal tract including aphthous ulcers, gingivitis, Crohn's disease (a condition of the small, and sometimes also of the large intestine), atrophic gastritis and gastritis varialoforme (conditions of the stomach), ulcerative colitis (a condition of the large intestine and sometimes the small intestine) coeliac disease (a condition of the small intestine), regional ileitis (a regional inflammatory condition of the terminal ileum), peptic ulceration (a condition of the stomach and duodenum) and irritable bowel syndrome; pyresis, pain;

and other conditions associated with inflammation, particularly those in which lipoxygenase and cyclooxygenase products are a factor.

For the above mentioned uses the dosage administered will, of course, vary with the compound employed, the mode of administration and the treatment desired. However, in general satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from 7.0 mg to 1,400 mg and unit dosage forms suitable for oral administration comprise from 2.0 mg to 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral, parenteral or topical administration. Thus the new compounds may be compounded with inorganic or organic, pharmaceutically acceptable adjuvants, diluents or carriers. Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

compositions in a form suitable for administration to the lung include aerosols, particularly pressurised aerosols;

compositions in a form suitable for administration to the skin include creams, e.g. oil-in-water emulsions or water-in-oil emulsion;

compositions in a form suitable for administration to the eye include drops and ointments.

We prefer the composition to contain up to 50% and more preferably up to 25% by weight of the compound of formula I, or of the pharmaceutically acceptable derivative thereof.

The compounds of formula I and pharmaceutically acceptable derivatives thereof have the advantage that they are less toxic, more efficacious, are longer acting, have a broader range of activity, are more potent, produce fewer side effects, are more easily absorbed or have other useful pharmacological properties, than compounds of similar structure.

When any one of $R_2$, $R_3$, $R_4$ and $R_5$ represents alkyl or any one of $Ar_1$, $Ar_2$ and $Ar$ is substituted by alkyl or alkanoyl, the alkyl or alkanoyl group preferably contains from 1 to 18 carbon atoms, more preferably 1 to 15 carbon atoms, particularly 1 to 12 carbon atoms. Particular alkyl groups that may be mentioned include saturated and unsaturated groups, for example, methyl, ethyl, allyl, propyl, buten-4-yl, hexyl, octyl, decyl, dodecyl and cetyl. Particular alkanoyl groups that may be mentioned include acetyl, hexanoyl, decanoyl, dodecanoyl and palmitoyl.

We prefer compounds of formula I in which $R_2$ represents $Ar_2$.

Aryl groups that $Ar_1$, $Ar_2$, $Ar_3$ and $Ar$ may each independently represent include carbocyclic and heterocyclic groups having aromatic character. The groups may be a single ring or a fused ring system, e.g. comprising from 2 to 4 rings and optionally containing one or more hetero atoms, for example nitrogen, oxygen or sulphur. Preferred aryl groups are those having from 5 to 10 ring selected from carbon, nitrogen, oxygen and sulphur.

Specific aryl groups that may be mentioned include phenyl, naphthalenyl, pyridinyl, quinolinoyl, furanyl, thiophenyl, pyrrolyl, indolyl, pyrimidinyl, thiazolinyl and benzthiazolinyl.

When $Ar_1$, $Ar_2$ or $Ar$ represent a substituted aryl group, $Ar_1$, $Ar_2$ or $Ar$ preferably bears one, two or three substituents, which may be the same or different, selected from halogen, e.g. fluorine, chlorine or bromine.

Halogen substituents that may be mentioned include fluorine, chlorine, bromine and iodine.

—$COR_6$ substituents that may be mentioned include those in which $R_6$ represents —OH; Oalkyl, e.g. O-methyl, O-ethyl or O-propyl; hydrogen, i.e. the substituent represents —$CHO_2$; alkyl, particularly alkyl C1 to 6, e.g. methyl or ethyl; —$NR_7R_8$, e.g. NHalkyl or N(alkyl)$_2$. Specific substituents that —$COR_6$ may represent include —COOH, —$COOH_3$, $COCH_3$ and $CON(C_2H_5)_2$.

Trihalomethyl substituents that may be mentioned include trichloromethyl and especially trifluoromethyl.

Substituents in which alkoxy is substituted by —$NR_7R_8$ that may be mentioned include those in which $NR_7R_8$ that may be mentioned include those in which $NR_7R_8$ represents $NH_2$, NHalkyl and N(alkyl)$_2$. Substituents that may be specifically mentioned include alkoxy C1 to 6 substituted by —N(alkyl)2, e.g. —$OCH_2CH_2N(C_2H_5)_2$.

Substituents in which alkoxy is substituted by —$COR_6$ that may be mentioned include those in which —$COR_6$ represents —COOH; —COOalkyl, e.g. —$COOCH_3$, —COalkyl, e.g. —$COCH_3$; and —$CONR_7R_8$, e.g. —$CON(C_2H_5)_2$.

Substituents in which alkoxy is substituted by $Ar_3$ that may be mentioned include those in which $Ar_3$ represents an aryl group having from 5 to 10 ring atoms selected from carbon, nitrogen, oxygen or sulphur. $Ar_3$ groups may be specifically mentioned are phenyl and pyridinyl.

Substituents in which alkyl is substituted by —$COR_6$ that may be mentioned include those in which $COR_6$ represents —COOH; COOalkyl, e.g. COOethyl or COOmethyl; —$CONR_7R_8$, e.g. —$CON(C_2H_5)_2$ and COalkyl, e.g. $COCH_3$. Specific substituents include alkyl C1 to 6 substituted by —COOH or —$COOC_2H_5$, e.g. —$CH_2COOH$.

Substituents in which alkyl is substituted by $NR_7R_8$ that may be mentioned include those in which $NR_7R_8$ represents $NH_2$, NHalkyl, N(alkyl)$_2$ and NHCOalkyl. Specific groups that may be mentioned include $CH_2N(C_2H_5)_2$.

$S(O)_nR_9$ substituents that may be mentioned include those in which n is 0, 1 or 2 and $R_9$ represents alkyl, such as Salkyl, e.g. $SCH_3$; SOalkyl, e.g. $SOCH_3$; and $SO_2$alkyl, e.g. $SO_2CH_3$.

$NR_7R_8$ substituents that may be mentioned include $NH_2$, NHalkyl, N(alkyl)$_2$ NHalkanoyl. Alkyl groups that $R_7$ or $R_8$ may each independently represent include methyl, ethyl, propyl and butyl. Alkanoyl groups that $R_7$ and $R_8$ may each independently represent include formyl, acetyl and proprionyl. Particular groups that —$NR_7R_8$ may represent are —$N(CH_3)_2$, —$N(C_2H_5)_2$ and —$NHCOCH_3$). Preferred groups that $Ar_1$, $Ar_2$, $Ar_3$ and Ar may represent include phenyl or pyridinyl, $Ar_1$, $Ar_2$, $Ar_3$ and Ar being optionally substituted, preferably by one or more of halogen, trihalomethyl or alkyl C1 to 6. A particularly preferred group is phenyl.

Preferred groups that $Ar_2$ may represent include phenyl, phenyl substituted by alkoxy, alkoxy C1 to 6 substituted by —$NR_7R_8$ or phenyl. Where the phenyl is substituted, the substituent is preferably in the 4-position.

Preferred groups that Ar may represent include phenyl and 2-, 3- or 4-pyridinyl. Ar is preferably in the 5-position of the pyrazole ring.

When $R_3$ represents alkyl, $R_3$ may represent pentyl or hexyl and especially methyl, ethyl, propyl or butyl.

We particularly prefer compounds in which $R_3$ represents hydrogen, alkyl C1 to 6 or benzyl.

We particularly prefer compounds in which $R_4$ and $R_5$, which may be the same or different, independently represent hydrogen, halogen, e.g. chlorine or bromine, alkyl, e.g. methyl or ethyl or alkyl substituted by an aryl group, the aryl group having from 5 to 10 ring atoms selected from carbon, nitrogen, oxygen and sulphur. Particular groups that $R_4$ and $R_5$ may represent include hydrogen, alkyl C1 to 6, e.g. methyl, phenyl, pyridinyl, dimethylaminophenyl, furanyl, thiophenyl, phenylalklyl, e.g. phenylethyl, and pyridinylalkyl, e.g. pyridinylethyl.

Certain of the compounds of formula I possess one or more chiral centres and the invention also provides the compounds in the form of their individual optical isomers or as racemic or other mixtures thereof. Certain of the compounds of formula I may also exist as stereoisomers and in these cases the invention provides all stereoisomeric forms. The various isomers may be prepared and/or separated using conventional processes known per se.

The invention is illustrated but in no way limited by the following Examples, in which temperatures are in degrees Celsius.

EXAMPLE 1

N-(4-Phenylmethoxyphenyl-1-phenyl-1H-pyrazol-3-amine (a)

4,5-Dihydro-N-(4-phenylmethoxyphenyl)-1-phenyl-1H-pyrazol-3-amine

A mixture of 1-phenyl-1H-pyrazolidin-3-one (8.1 g), 4-phenylmethoxyaniline (20 g) and 4-toluenesulphonic acid (5 g) was heated in an oil bath at 140° under a nitrogen atmosphere for 15 minutes. The reaction was cooled and the products dissolved in 1% sodium hydroxide solution and ether. The organic phase was separated and washed with 1% hydrochloric acid solution, water and then dried over sodium sulphate. The organic phase was filtered and evaporated to a pale oil which on trituration with pentane gave the sub-title compound (6.0 g), mp 187°–188°.

(b)

N-(4-Phenylmethoxyphenyl)-1-phenyl-1H-pyrazol-3-amine

Manganese dioxide (2.5 g) was added portionwise over 10–15 minutes to a solution of the product of step (a) (3.43 g) in dichloromethane (300 ml) stirred at room temperature. After stirring for an additional 30 minutes at room temperature, the reaction mixture was filtered, solvent was removed and the resulting gum was chromatographed on silica gel eluting with dichloromethane: ethyl acetate (95:5) to give the title compound (2.45 g) mp 145°–146°.

Found: C:77.63, H:5.51, N:12.22%. $C_{22}H_{19}N_3O$ requires: C:77.41, H:5.58, N:12.31%.

EXAMPLE 2

N-(4-Methoxyphenyl)-1-phenyl-1H-pyrazol-3-amine (a)

4,5-Dihydro-N-(4-methoxyphenyl)-1-phenyl-1H-pyrazol-3-amine

A mixture of 4,5-dihydro-1-phenyl-1H-pyrazol-3-amine (32.2 g), 4-methoxyaniline (27.0 g) and 4-toluenesulphonic acid, (1.0 g) was heated at 160°–170° for 2 hours.

The mixture was cooled and dichloromethane was added. The organic phase was washed with diluted hydrochloric acid, dried and evaporated to give the sub-title compound (5.0 g), mp 153°–154°.

Found: C:71.41; H:6.3; N:15.74%. C$_{16}$H$_{17}$N$_3$O: C:71.41; H:6.41; N:15.73%.

(b) N-(4-Methoxyphenyl)-1-phenyl-1H-pyrazol-3-amine 4,5-Dihydro-N-(4-methoxyphenyl)-1-phenyl-1H-pyrazol-3amine (50 g) was dissolved in dichloromethane (500 ml) and treated portionwise with activated manganese dioxide (50 g) over one hour. The mixture was stirred for a further 2 hours then filtered through bentonite and chromatographed on a silica column with dichloromethane as eluant. The eluants were evaporated to dryness and the title compound recrystallised from aqueous ethanol as an off-white solid (40 g), mp 96°–98°.

Found: C:72.45; H:5.74; N:15.84%. C$_{15}$H$_{15}$N$_3$O Requires: C:72.45; H:5.62; N:15.82%.

EXAMPLE 3

(a) The following N-1,diaryl-4,5-dihydro-1H-pyrazol-3-amines were prepared by the method of Example 2a, from the appropriately substituted 1-aryl-4,5-dihydro-1 H-pyrazol-3-amines and arylamines:

4,5-Dihydro-N-(4-methoxyphenyl)-1-(4-methylphenyl)-1H-pyrazol-3-amine, mp 163°–165°;
4-(4,5-Dihydro-1-phenyl-1H-pyrazol-3-yl)aminobenzoic acid, mp 232°–235°;
4,5-Dihydro-N-methyl-1,N-diphenyl-1H-pyrazol-3-amine, mp 100°–102°;
4,5-Dihydro-N-(4-dimethylaminophenyl)-1-phenyl-1H-pyrazol-3-amine, mp 142°–143°;
1-(4—Chlorophenyl)-4,5-dihydro-N-(3-pyridinyl)-1H-pyrazol-3-amine, mp 234°–236°;
1-(4—Chlorophenyl)-4,5-dihydro-N-(4-methylpyridin)-2-yl)-1H-pyrazol-3-amine, mp 208°–210°;
4,5-Dihydro-1,N-diphenyl-1H-pyrazol-3-amine, mp 155°–156°;
(±)-4,5-Dihydro-N-(4-methoxyphenyl)-4-methyl-1-phenyl-1H-pyrazol-3-amine, mp 97°–100°;
(±)-4,5-Dihydro-N-(4-methoxyphenyl)-5-methyl-1-phenyl -1H-pyrazol-3-amine, mp 47°–50°;
1-(3-Trifluoromethylphenyl)-4,5-dihydro-N-phenyl-1H-pyrazol-3-amine, mp 128°–129°;
1-(3-Trifluoromethylphenyl)-4,5-dihydro-N-(3-pyridinyl)-1H-pyrazol-3-amine, mp 235°–237° (dec);
1-(4—Chlorophenyl)-4,5-dihydro-N-(4-methoxyphenyl)-1H-pyrazol-3-amine, mp 145°–146°;
Ethyl 4-(4,5-dihydro-1-[4-methylphenyl]-1H-pyrazol -3-yl)aminophenylacetate;
4,5-Dihydro-1-(4-methoxyphenyl)-N-phenyl-1H-pyrazol-3amine, mp 145°–146°;
Ethyl 4-[4,5-dihydro-1-phenyl-1H-pyrazol-3-yl]amino phenylacetate;
4,5-Dihydro-N-(3-methoxyphenyl)-1-phenyl-1H-pyrazol -3-amine, mp 115°–117°;
Methyl 4-(4,5-dihydro-1-phenyl-1H-pyrazol-3-yl) aminobenzoate;
N,N-diethyl-4-(4,5-dihydro-1-phenyl-1H-pyrazol-3yl)-aminobenzamide, mp 235°–238° (dec);
4,5-Dihydro-N-(4-methoxyphenyl)-N-methyl-1-phenyl-1H-pyrazol-3-amine, mp 105°–107°;
4,5-Dihydro-N-(2-methoxypyridin-5-yl)-1--phenyl-1H-pyrazol-3-amine, mp 186°–187°;
(±) 4,5-Dihydro-N-(4-methoxyphenyl)-1,5-diphenyl-1H-pyrazol-3-amine, mp 186°–188°;
4,5-Dihydro-N-(2-methylphenyl)-1-phenyl-1H-pyrazol-3-amine, mp 133°–135°;
4,5-Dihydro-N-(4-methoxyphenyl)-1-phenyl-1H-pyrazol-3-amine, mp 157°–159°;
1-(3-Trifluoromethylphenyl)-4,5-dihydro-N-(4-methoxyphenyl)-1H-pyrazol-3-amine, mp 127°–128°.
N-(3-Acetyl-4-methoxyphenyl)-4,5-dihydro-1-phenyl-1H-pyrazol-3-amine;
4,5-Dihydro-N-(4-methoxyphenyl)-1-(2-pyridinyl)-1H-pyrazol-3-amine;
N-(4-Aminophenyl)-4,5-dihydro-1-phenyl-1H-pyrazol-3-amine;
N-[4-(4,5-dihydro-1-phenyl-1H-pyrazol-3-yl)aminophenyl]acetamide;
4,5-Dihydro-1,N-Bis-(4-methoxyphenyl)-1H-pyrazol-3-amine;
4,5-Dihydro-N-(3-dimethylaminophenyl)-1-phenyl-1H-pyrazole-3-amine;
4,5-Dihydro-N-(4-methylphenyl)-1-phenyl-1H-pyrazol-3-amine, mp 154°–156°;
N-(4—Chlorophenyl)-4,5-dihydro-1-phenyl-1H-pyrazol-3-amine, mp 144°–147°;
4,5-Dihydro-N-(3,4-dimethoxyphenyl)-1-phenyl-1H-pyrazol-3-amine, mp 150°–152°;
(±)-4,5-Dihydro-N-(4-methoxyphenyl)-1-phenyl-5-(3-pyridinyl)-1H-pyrazol-3-amine;
4,5-Dihydro-N-(4-methoxyphenyl)-1-(3-pyridinyl)-1H-pyrazol-3-amine;
4,5-Dihydro-N-(4-methylthiophenyl)-1-phenyl-1H-pyrazol-3-amine, mp 116°–119°;
(±)-5-(4-Dimethylaminophenyl)-4,5-dihydro-N-(4-methoxyphenyl)-1-phenyl-1H-pyrazol-3-amine;
4,5-Dihydro-N-(4-methoxyphenyl)-1-[4-(phenylmethoxy)phenyl]-1H-pyrazol-3-amine;
4-(4,5-Dihydro-1-phenyl-1H-pyrazol-3-yl)aminobenzonitrile;
4,5-Dihydro-1-(4-fluorophenyl)-N-(4-methoxyphenyl)-1H-pyrazol-3-amine, mp 156°–158°;
(2-Benzthiazolyl-)-4,5-dihydro-1-N-(4-methoxyphenyl)-1H-pyrazol-3-amine, mp 223°–226° (decomp);
4,5-Dihydro-N-(4-phenoxyphenyl)-1-phenyl-1H-pyrazol -3-amine;
(±)-4,5-Dihydro-5-(2-furanyl)-N-(4-methoxyphenyl)-1-phenyl-1H-pyrazol-3-amine, mp 114°–116°;
4,5-Dihydro-N-(4-phenylaminophenyl)-1-phenyl-1H-pyrazol-3-amine;
(±)-4,5-Dihydro-N-(4-methoxyphenyl)-1-phenyl-5-(thien-2-yl)-1H-pyrazol-3-amine;
(±)-4,5-Dihydro-N-(4-methoxyphenyl)-1-phenyl -5-(2-phenyl-ethyl)-1H-pyrazol-3-amine;
(±)-3-(2-[4,5-Dihydro-3 4-methoxyphenylamino -1-phenyl-1H-pyrazol-5-yl-]ethyl)pyridine;
4,5-Dihydro-N-(4-methoxyphenyl)-1-(2-naphthalenyl-1H-pyrazol-3-amine, mp 166°–168°;
4-[4,5-Dihydro-3-(4-methoxyphenylamino)-1H-pyrazol -1-yl]-6-methylpyrimidine, mp 199°–200°;
5-(4,5-Dihydro-1-phenyl-1H-pyrazol-3-yl)amino-1H-indole;
4,5-dihydro-N-(3-hydroxy-4-propylphenyl)-1-phenyl-1H -pyrazol-3-amine, mp 167°–170°;
(±)-4,5-dihydro-1,5-diphenyl-N-(3-pyridinyl)-1H-pyrazol-3-amine, mp 168°–170°.

(b) The following compounds of formula I were prepared by oxidation of the corresponding 1,N-diaryl-dihydro-1H -pyrazol-3-amines by the method of Example 2(b):

(1) N-(4-Methoxyphenyl)-1-(4-methylphenyl)-1H-pyrazol-3-amine, mp 108°–109°;
(2) 4-(1-Phenyl-1H-pyrazol-3-yl)aminobenzoic acid, mp 220°–221°;
(3) N-Methyl-1,N-diphenyl-1H-pyrazol-3-amine, mp 77°–79°;
(4) N-(4-Dimethylaminophenyl)-1-phenyl-1H-pyrazol-3-amine, mp 115°–117°;
(5) 1-(4—Chlorophenyl)-N-(3-pyridinyl)-1H-pyrazol-3-amine, mp 216°–218°;
(6) 1-(4—Chlorophenyl)-N-(4-methylpyridin-2-yl)-1H-pyrazol -3-amine, mp 173°–175°;
(7) 1,5-Diphenyl-N-(3-pyridinyl)-1H-pyrazol-3-amine, mp 172°–174°;
(8) 1,5,N-Triphenyl-1H-pyrazol-3-amine, mp 113°–115°;
(9) 1,N-Diphenyl-1H-pyrazol-3-amine, mp 88°–91°;
(10) N-(4-Methoxyphenyl)-4-methyl-1-phenyl-1H-pyrazol-3-amine, mp 110°–111°;
(11) N-(4-Methoxyphenyl)-5-methyl-1-phenyl-1H-pyrazol-3-amine, mp 111°–113°;
(12) 1-(3-Trifluoromethylphenyl)-N-phenyl-1H-pyrazol-3-amine, mp 99°–101°;
(13) 1-(3-Trifluoromethylphenyl)-N-(3-pyridinyl)-1-H-pyrazol-3-amine, mp 170°–171°;
(14) Ethyl 4-(1-[4-methylphenyl]-1H-pyrazol-3-yl)aminophenylacetate, oil;
(15) 1-(4-Methoxyphenyl)-N-phenyl-1H-pyrazol-3-amine mp 143°–144°;
(16) Ethyl 4-(1-phenyl-1H-pyrazol-3-yl)aminophenylacetate, mp 154°–156°;
(17) N-(3-Methoxyphenyl)-1-phenyl-1H-pyrazol-3-amine, mp 123°–5°.
(18) 4-(3-Phenylamino-1H-pyrazol-1-yl)phenol, mp 185°–187°;
(19) Methyl 4-(1-phenyl-1H-pyrazol-3-yl)aminobenzoate, mp 160°–161°;
(20) N,N-Diethyl-4-[(1-phenyl-1H-pyrazol-3-yl)amino]benzamide, mp 167°–168°.
(21) N-(4-Methoxyphenyl)-N-methyl-1-phenyl-1H-pyrazol-3amine, mp 102°–103°;
(22) N-(2-Methoxypyridin-5-yl)-1-phenyl-1H-pyrazol-3-amine, hemihydrate, mp 126°–128°;
(23) N-(4-Methoxyphenyl)-1,5-diphenyl-1H-pyrazol-3-amine, mp 172°–173°;
(24) N-(2-Methylphenyl)-1-phenyl-1H-pyrazol-3-amine, (oil);
(25) N-(2-Methoxyphenyl)-1-phenyl-1H-pyrazol-3-amine, (oil);
(26) N-(3-Acetyl-4-methoxyphenyl)-1-phenyl-1H-pyrazol-3-amine, mp 178°–180°;
(27) 1-(4—Chlorophenyl)-N-(4-methoxyphenyl)-1H-pyrazol-3-amine, mp 130°;
(28) N-(4-Methoxyphenyl)-1-(3-trifluoromethylphenyl)-1-H-pyrazol-3-amine, mp 87°–88°;
(29) N-(4-Methoxyphenyl)-1-(2-pyridinyl)-1H-pyrazol-3-amine, mp 121°–122°;
(30) N-(4-Aminophenyl)-1-phenyl-1H-pyrazol-3-amine, mp 106°–108°;
(31) N-[4-(1-Phenyl-1H-pyrazol-3-yl)aminophenyl]acetamide, mp 187°–189°;
(32) 1,N-Bis-(4-methoxyphenyl)-1H-pyrazol-3-amine, mp 134°–136°;
(33) N-(3-Dimethylaminophenyl)-1-phenyl-1H-pyrazole-3-amine, mp 99°–101°;
(34) N-(4-Methylphenyl)-1-phenyl-1H-pyrazol-3-amine, mp 108°–110°;
(35) N-(4—Chlorophenyl)-1-phenyl-1H-pyrazol-3-amine, mp 105°–107°;
(36) N-(3,4-Dimethoxyphenyl)-1-phenyl-1H-pyrazol-3-amine mp 94°–95°;
(37) N-(4-Methoxyphenyl)-1-phenyl-5-(3-pyridinyl)-1-H-pyrazol-3-amine, mp 172°–173°;
(38) N-(4-Methoxyphenyl)-1-(3-pyridinyl)-1H-pyrazol-3-amine, mp 157°–160°;
(39) N-(4-Methylthiophenyl)-1-phenyl-1H-pyrazol-3-amine, mp 120°–122°;
(40) 5-(4-Dimethylaminophenyl)-N-(4-methoxyphenyl)-1-phenyl -1H-pyrazol-3-amine, mp 173°–174°;
(41) N-(4-Methoxyphenyl)-1-[4-(phenylmethoxy)phenyl]-1-H-pyrazol-3-amine, mp 134°–136°;
(42) 4-(1-Phenyl-1H-pyrazol-3-yl)aminobenzonitrile, mp 150°–153°;
(43) N-(4-Methoxyphenyl)-1-(2-pyridinyl)-1H-pyrazol-3-amine, mp 121°–122°;
(44) N-(4-Methoxyphenyl)-1-(3-trifluoromethylphenyl)-1H-pyrazol-3-amine, mp 87°–88°;
(45) 1-(4-Fluorophenyl)-N-(4-methoxyphenyl)-1H-pyrazol -3-amine, mp 107°–109°;
(46) 1-(2-Benzthiazolyl)-N-(4-methoxyphenyl)1H-pyrazol-3-amine, mp 160°–162°;
(47) N-(4-Phenoxyphenyl)-1-phenyl-1H-pyrazol-3-amine, mp 76°–78°;
(48) 5-(2-Furanyl)-N-(4-methoxyphenyl)-1-phenyl-1H-pyrazol-3-amine, mp 115°–116°;
(49) N-(4-Phenylaminophenyl)-1-phenyl-1H-pyrazol-3-amine, mp 122°–123°;
(50) N-(4-Methoxyphenyl)-1-phenyl-5-(thien-2-yl)-1H-pyrazol -3-amine, mp 131°–133°;
(51) N-(4-Methoxyphenyl)-1-phenyl-5-(2-phenylethyl)-1H-pyrazol-3-amine, mp 87°–89°;
(52) 3-(2-[3-{4-Methoxyphenylamino}-1-phenyl-1H-pyrazol-5-yl]ethyl)pyridine, mp 109°;
(53) N-(3-Hydroxy-4-propylphenyl)-1-phenyl-1H-pyrazol-3-amine, mp 118°–119°;
(54) N-(4-Methoxyphenyl)-1-(2-naphthalenyl)-1H-pyrazol-3-amine, mp 151°–152°;
(55) 4-[3-(4-Methoxyphenylamino)-1H-pyrazol-1-yl]-6-methylpyrimidine, mp 127°–129° (dec);
(56) 5-(1-Phenyl-1H-pyrazol-3-yl)amino-1H-indole, mp 139°–141°.
(57) 1-(3-Trifluoromethylphenyl)-3-(1-pyrrollidinyl) -pyrazole hydrochloride, mp 154°–156°;
(58) N-Benzyl-1-(3-trifluoromethylphenyl)-1H-pyrazole-3-amine hydrochloride, mp 158°–160°;
(59) N-(4-Decyloxyphenyl)-1-phenyl-1H-pyrazol-3-amine, mp 92°–93°;
(60) N-(4-Methoxyphenyl)-1-(3-quinolinyl)-1H-pyrazol -3-amine.

EXAMPLE 4

4-(1-Phenyl-1H-pyrazol-3-yl)aminophenol

A suspension of N-(4-benzyloxyphenyl)-1-phenyl-1-H-pyrazol-3-amine (3.17 g) in ethanol (600 ml) was hydrogenated at atmospheric pressure over 10% palladium on carbon until hydrogen uptake ceased. The reaction mixture was filtered and solvent was evaporated. The resulting solid was recrystallised from ether: petroleum ether to give the title compound (1.3 g) mp 147°–148°.

Found: C 71.61, H: 5.31, N: 16.67%. $C_{15}H_{13}N_3O$ requires: C 71.71, H: 5.22, N: 16.73%.

EXAMPLE 5

The following compound was prepared by the method of Example 4:
(1) 4-[3-(4-Methoxyphenylamino)-1H-pyrazol-1-yl]phenol, mp 192°–194°;

EXAMPLE 6

N-[4-(2-Diethylaminoethoxy)phenyl]-1-phenyl-1H-pyrazol-3-amine

Potassium carbonate (2.25 g), the product of Example 4 (2.02 g) and 2-diethylaminoethylchloride hydrochloride (1.39 g) in dimethylformamide (30 ml) were stirred together at room temperature for 36 hours. The reaction mixture was then diluted with water and extracted with ethyl acetate. The combined extracts were washed with water and dried. Solvent was removed to give an oil (2.4 g) which was redissolved in ether (50 ml) and a solution of fumaric acid (0.80 g) in ether (480 ml) was added to give a precipitate, which was collected and dried to give the 2E-butenedioate of the title compound (1.88 g) mp 58°–63° (dec).

Found: C: 63.45; H: 6.52; N: 11.82; $H_2O$: 1.8%. $C_{25}H_{30}N_4O_5$. 0 5 $H_2O$ Requires: C: 63.16, H: 6.32, N: 11.78, $H_2O$: 1.8%.

EXAMPLE 7

The following compounds were prepared by the method of Example 6:
(1) Ethyl 4-[3-(4-methoxyphenylamino)-1H-pyrazol-1-yl]phenoxyacetate, mp 91°–92°;
(2) Ethyl 4-[1-phenyl-1H-pyrazol-3-yl]aminophenoxy acetate;
(3) 1-[4-2-Diethylaminoethoxy)phenyl]-N-(4-methoxyphenyl-1H-pyrazol-3-amine, mp 66°.

EXAMPLE 8

4-[3-(4-Methoxyphenylamino)-1H-pyrazol-1-yl]phenoxyacetic acid

Ethyl 4-[3-(4-methoxyphenylamino)-1H-pyrazol-1-yl]phenoxyacetate (1.0 g) in ethanol (200 ml) and 10% sodium hydroxide (5 ml) was heated to reflux for 1 hour. Upon cooling, the resultant pink solid was filtered off and treated with a little 10% hydrochloric acid to give a violet solid which was filtered off, rinsed with water and dried to give the title compound (0.85 g), mp 163°–165°.

Analysis: Water content=1.1% by thermogravimetric analysis.

Found: C 62.96; H: 5.17; N: 12.23%. $C_{18}H_{17}N_3O_4$ 0.25$H_2O$ Requires: C: 63.02; H: 5.07; N: 12.25%. and water content 1.3%

EXAMPLE 9

The following compounds were prepared by the method of Example 8:
(1) 4-(1-[4-Methylphenyl]-1H-pyrazol-3-yl)aminophenylacetic acid hemihydrate, mp 172°–174°;
(2) 4-(1-Phenyl-1H-pyrazol-3-yl)aminophenylacetic acid, mp 205°–207°;
(3) 4-[1-Phenyl-1H-pyrazol-3-yl]aminophenoxyacetic acid, mp 186°–188°.

EXAMPLE 10

4-(3-Phenylamino-1H-pyrazol- 1-yl)phenol 1-(4-Methoxypheny-1)-N-phenyl-1H-pyrazol-3-amine (6.7 g) and 45% hydrobromic acid in acetic acid (80 ml) were heated at 100° for 10 hours. The cool solution was poured into water and 10% sodium hydroxide added to pH 5; then the mixture was basified further with saturated sodium bicarbonate solution to pH 9. The mixture was extracted with ether (200 ml), which was dried and treated with cyclohexane (50 ml). The solution was evaporated on a steam bath until precipitation started. The solution was left to cool and the resultant solid collected by filtration to give the title compound (4.0 g), mp 182°–185°;

Analysis: Found: C: 71 33; H: 5.27; N: 16.56%. $C_{15}H_{13}N_3O$ Requires: C: 71.71; H: 5.18; N: 16.73%.

EXAMPLE 11

N-[(4-Diethylaminomethyl)phenyl]-1-phenyl-1H-pyrazol-3-amine

A solution of N,N-diethyl-4-[(1-phenyl-1H-pyrazol-3-yl)amino]benzamide (0.93 g) in dry tetrahydrofuran (40 ml) was added to a suspension of lithium aluminium hydride (0.23 g) in dry tetrahydrofuran (40 ml). The resulting mixture was heated to reflux under nitrogen for 3 hours. After cooling to room temperature, a saturated solution of sodium sulphate was added to give a precipitate, the supernatant decanted and the precipitate washed with ether. The washings and supernatant were combined and extracted with dilute hydrochloric acid. Excess saturated aqueous sodium bicarbonate solution was added to the resulting aqueous layer, which was extracted with ethyl acetate. The resulting organic layer was separated and washed with water followed by saturated sodium chloride solution, and dried. Solvent was removed to give an oil (0.72 g) which was redissolved in ether (50 ml) and a solution of fumaric acid (0.27 g) in ether (177 ml) was added. The resulting precipitate was collected and dried to give the 2E-butenedioate of the title compound (0.78 g), mp 110°–116° (dec.);

Found: C: 63.89, H: 6.08; N: 12.54; $H_2O$: 2.83%. $C_{24}H_{28}N_4O_4\frac{1}{2}$ $H_2O$ Requires: C: 64.18; H: 6.28; N: 12.48; $H_2O$: 2.8%.

EXAMPLE 12

N-(3-Acetyl-4-hydroxyphenyl)-1-phenyl-1H-pyrazol-3-amine (a) 4-[1-Phenyl-1H-pyrazol-3-yl]aminophenyl ethanoate A mixture of 4-(1-phenyl-1H-pyrazol-3-yl)aminophenol (2.0 g), acetic anhydride (4 g) and sulphuric acid (0.2 g) was heated at 100° C. on the steam bath for 15 minutes, water was added and the product was collected by filtration and dried to give the sub-title compound (2.0 g) as a brown solid.

(b) N-(3-Acetyl-4-hydroxyphenyl)-1-phenyl-1H-pyrazol-3-amine

A mixture of 4-[1-phenyl-1H-pyrazol-3-yl]aminophenyl ethanoate (2.0 g) and aluminium chloride (3.0 g) was heated at 140° for 3 hours, water was added and the aqueous phase was extracted into dichloromethane. The organic phase was purified by chromatography on a silica column using dichloromethane as eluant. Evaporation of solvents gave the title compound as a colourless solid (0.5 g), mp 165°–167°.

Analysis: Found: C: 69.54; H: 5.25; N: 14.0% $C_{17}H_{15}N_3O_2$ Requires: C: 69.3; H: 5.1; N: 14.3%

EXAMPLE 13

N-(4-Methylsulphonylphenyl)-1-phenyl-1H-pyrazol-3-amine

To a solution of N-(4-methylthiophenyl)-1-phenyl-1H-pyrazol-3-amine (1.4 g) in dichloromethane (100 ml) was added a solution of 3-chloroperbenzoic acid (2.0 g) in dichloromethane (20 ml) and the mixture stirred at room temperature for 1 hour. The solution was washed with dilute sodium hydroxide solution, dried over magnesium sulphate, filtered and evaporated to dryness to leave the colourless title compound (1.2 g) mp 185°-187°;

Analysis: Found: C: 60.98; H: 4.71, N: 13.26%. $C_{16}H_{15}N_3O_2S$ Requires: C: 61.32; H: 4;82, N: 13.41%.

EXAMPLE 14

N-(4-Methylsulphinylphenyl)-1-phenyl-1H-pyrazol-3-amine

To a solution of N-(4-methylthiophenyl)-1-phenyl-1-H-pyrazol-3-amine (1.4 g) in dichloromethane (100 ml) at 0° was added a solution of 3-chloroperbenzoic acid (0.9 g) in dichloromethane (20 ml) and the mixture stirred and allowed to reach room temperature over 1 hour. The solution was washed with dilute sodium hydroxide solution, dried over magnesium sulphate, filtered and evaporated to an oil. The oil was dissolved in hot ether and gradual evaporation to a small volume gave the title compound as a colourless solid (1.2 g), collected by filtration, mp 123°-124°.

Analysis: Found: C: 64.71; H: 5.18; N: 14.10%. $C_{16}H_{15}N_3OS$ Requires: C: 64.64; H: 5.05; N: 14.4%.

EXAMPLE 15

2-(1-Phenyl-1H-pyrazol-3-yl)aminothiazol-4-ol

A solution of N-(1-phenyl-1H-pyrazol-3-yl)thiourea (4.2 g) and ethyl 2-chloroethanoate (3.0 g) in ethyl alcohol (50 ml) was heated under reflux for 2 hours. The mixture was cooled and the title compound collected by filtration as a yellow solid 4.0 g, mp >230°.

Analysis: Found: C: 55.5; H: 3.98; N: 21.5%. $C_{12}H_{10}N_4OS$ Requires: C: 55.8; H: 3.88; N: 21.7%.

EXAMPLE 16

5 Chloro-N-(4-methoxyphenyl)-1-phenyl-1H-pyrazol-3-amine

A mixture of 5-(4-methoxyphenylamino)-2-phenyl-pyrazolidin-3-one (2.81 g) and excess phosphorous oxychloride (4 ml) was heated on a steam bath at 100° for 1 hour. Water was added and the aqueous phase extracted with dichloromethane. The organic phase was dried over magnesium sulphate, filtered and evaporated to dryness, and the title compound was obtained as a colourless solid (1.5 g), mp 119°-121° by recrystallisation from cyclohexane.

Analysis: Found: C: 64.14; H: 4.54; N: 13.92%. $C_{16}H_{14}N_3O$ Requires: C: 64.00; H: 4.66; N: 14.00%.

EXAMPLE 17

N-(4-Methoxyphenyl)-1-phenyl-1H-pyrazol-3-amine

A solution of 5-chloro-N-(4-methoxyphenyl)-1-phenyl-1H-pyrazol-3-amine (0.2 g) in ethanol (10 ml) and triethylamine (0.2 g) was reduced at atmospheric pressure of hydrogen over 10% palladium/charcoal (0.2 g), with stirring, over 3 hours. The solution was filtered and evaporated to leave the title compound as a colourless solid, mp 96°-98°, the NMR and mass spectra of which were identical to those for the title compound of Example 2.

EXAMPLE 18

N-(4-Methoxyphenyl)-5-methyl-1-phenyl-1H-pyrazol-3-amine

N-(4-Methoxyphenyl)-5-methyl-1H-pyrazol-3-amine (0.05 g) in dry dimethylformamide (1 ml) was added to a stirred suspension of sodium hydride (0.015 g of a 50% oil dispersion), freed from oil, in dimethylformamide (0.5 ml). After 10 minutes diphenyliodonium chloride (0.102 g) was added. After 16 hours the mixture was diluted with water and extracted with ethylacetate, which was then dried and evaporated. The resultant oil was chromatographed on silica with dichloromethane containing 3% ethyl acetate to give the title compound (0.002 g), the NMR, mass and IR spectra, and TLC behaviour, of which were identical to those of the compoud of Example 3.11.

EXAMPLE 19

Methyl 4-(1-phenyl-1H-pyrazol-3-yl)aminobenzoate 4-(1-Phenyl-1H-pyrazol-3-yl)aminobenzoic acid (0.110 g) in dry dichloromethane was treated with an excess of ethereal diazomethane. After 5 minutes the solvents were evaporated to yield the title compound, mp 160°-161°.

PREPARATION OF INTERMEDIATES

Example A

(±)-4,5-Dihydro-1-phenyl-5-(3-pyridinyl)-1H-pyrazol-3-amine

Phenylhydrazine (7.6 g) was added to sodium (1.6 g) dissolved in dry ethanol (100 ml) and the mixture refluxed for 0.5 hour. The solution was cooled, 3-picolylideneacrylonitrile (9.1 g) was added and the resultant precipitate was filtered off, rinsed with a little ethanol, and then ether to give the title compound as a pale yellow powder (5.9 g), mp 185°-187°.

Similarly were prepared:
(1) 4,5-Dihydro-1-(3-pyridinyl)-1H-pyrazol-3-amine, mp 167°-170°.
(2) (+)4,5-Dihydro-5-(4-dimethylaminophenyl)-1-phenyl-1H-pyrazol-3-amine, mp 165°.
(3) (+)4,5-Dihydro-5-(2-furanyl)-1-phenyl-1H-pyrazol-3-amine;
(4) (±)4,5-Dihydro-1-phenyl-5-(2-thienyl)-1H-pyrazol-3-amine;
(5) (±)4,5-Dihydro-1-phenyl-5-(2-phenylethyl)-1H-pyrazol-3-amine;
(6) (±)3-(2- 3-amino-4,5-dihydro-1-phenyl-1H-pyrazol-5-yl ethyl)pyridine.

Example B

5-(3-pyridinyl)pent-2-enenitrile

A 50% w/w sodium hydride suspension in oil (1.87 g) was washed with petroleum ether (bp 40°-60°) and the stirred in dry tetrahydrofuran (50 ml) at 5°. To this suspension, diethylcyanophosphonate (6.9 g) in dry tetrahydrofuran (10 ml) was added dropwise. The resulting clear solution was stirred for 15 minutes before the dropwise addition of 3-(3-pyridinyl)propionaldehyde (5.2 g) in dry tetrahydrofuran (20 ml). The reaction was stirred for 45 minutes at room temperature, poured into water, and extracted with ethyl acetate.

The organic extracts were washed with water, dried and evaporated to give a brown oil (4.4 g). Gas chromatography - mass spectrometry showed the oil consisted of the trans and cis isomers (m/e of both=158) of the title nitrile in the ratio 5:3.

Similarly by the method of Example B were prepared:

5-Phenyl-pent-2-enenitrile (E:Z, 2:1).

We claim:

1. A composition for treating an inflammatory condition comprising an effective amount of a compound of formula I,

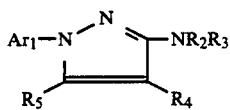

in which $R_2$ represents $Ar_2$;

$R_3$ represents hydrogen, alkyl $C_1$ to $C_{18}$ or alkyl $C_1$ to $C_{18}$ substituted by $Ar_3$;

$R_4$ and $R_5$, which may be the same or different, each independently represent hydrogen, halogen, Ar, alkyl $C_1$ to $C_{18}$ or alkyl $C_1$ to $C_{18}$ substituted by Ar, $Ar_1$, $Ar_2$ and Ar, which may be the same or different, each independently represent phenyl, naphthyl or either thereof substituted by one or more of halogen, hydroxy, —CN, —COR$_6$, trihalomethyl, alkoxy, alkoxy substituted by —COR$_6$, alkoxy substituted by —NR$_7$R$_8$, alkyl $C_1$ to $C_{18}$, alkyl $C_1$ to $C_{18}$ substituted by —COR$_6$, alkyl $C_1$ to $C_{18}$ substituted by NR$_7$R$_8$, alkoxy substituted by Ar$_3$, S(O)$_n$R$_9$, —NR$_7$R$_8$ or OAr$_3$;

$R_6$ represents —OR$_{10}$, —NR$_7$R$_8$, hydrogen or alkyl $C_1$ to $C_{18}$;

$R_7$ and $R_8$, which may be the same or different, each independently represent hydrogen, alkyl $C_1$ to $C_{18}$, alkanoyl $C_1$ to $C_{18}$ or Ar$_3$;

$R_9$ represents alkyl $C_1$ to $C_{18}$ or Ar$_3$;

$R_{10}$ represents hydrogen, alkyl $C_1$ to $C_{18}$ or Ar$_3$;

m represents an integer from 3 to 6 inclusive;

n represents 0, 1 or 2; and

Ar$_3$ represents unsubstituted phenyl or naphthyl; or a pharmaceutically acceptable acid addition, alkali metal, or alkaline earth metal salt thereof, in admixture with a pharmaceutically acceptable carrier, diluent or adjuvant.

2. A composition according to claim 1, wherein Ar$_2$ represents alkoxyphenyl.

3. A composition according to claim 1, wherein the compound of formula I is:
N-(4-methoxyphenyl)-1-phenyl-1H-pyrazol-3-amine.

4. A composition according to claim 1, wherein the compound of formula I is:
N-(4-Phenylmethoxyphenyl)-1-phenyl-1H-pyrazol-3-amine;
N-(4-Methoxyphenyl)-1-(4-methylphenyl)-1H-pyrazol-3-amine;
4-(1-Phenyl-1H-pyrazol-3-yl)aminobenzoic acid,;
N-methyl-1,N-diphenyl-1H-pyrazol-3-amine;
N-(4-Dimethylaminophenyl)-1-phenyl-1H-pyrazol-3-amine;
1,5,N-Triphenyl-1H-pyrazol-3-amine;
1,N-Diphenyl-1H-pyrazol-3-amine;
N-(4-Methoxphenyl)-4-methyl-1-phenyl-1H-pyrazol-3-amine;
N-(4-Methoxyphenyl)-5-methyl-1-phenyl-1H-pyrazol-3-amine;
1-(3-Trifluoromethylphenyl)-N-phenyl-1H-pyrazol)-3-amine;
Ethyl 4-(1-[4-methylphenyl]-1H-pyrazol-30yl)-aminophenylacetate;
1-(4-Methoxyphenyl)-N-phenyl-1H-pyrazol-3-amine;
Ethyl 4-(1-phenyl-1H-pyrazol-3-yl)aminophenyl acetate;
N-(3-Methoxyphenyl)-1-phenyl-1H-pyrazol-3-amine;
4-(3-Phenylamino-1H-pyrazol-1-yl)phenol;
Methyl 4-(1-phenyl-1H-pyrazol-3-yl)aminobenzoate;
N,N-Diethyl-4-[(1-phenyl-1H-pyrazol-3-yl)amino]-benzamide;
N-(4-Methoxyphenyl)-N-methyl-1-phenyl-1H-pyrazol-3-amine;
N-(4-Methoxyphenyl)-1,5-diphenyl-1H-pyrazol-3-amine;
N-(2-Methoxyphenyl)-1-phenyl-1H-pyrazol-3-amine;
N-(2-Methoxyphenyl)-1-phenyl-1H-pyrazol-3-amine;
N-(3-Acetyl-4-methoxyphenyl)-1-phenyl-1H-pyrazol-3-amine;
1-(4-Chlorophenyl)-N-(4-methoxyphenyl)-1H-pyrazol-3-amine;
N-(4-Methoxyphenyl)-1-(3-trifluoromethylphenyl)-1H-pyrazol-3-amine;
N-(4-Aminophenyl)-1-phenyl-1H-pyrazol-3-amine;
N-[4-(1-Phenyl-1H-pyrazol-3-yl)aminophenyl]-acetamide;
1,N-Bis-(4-methoxyphenyl)-1H-pyrazol-3-amine;
N-(3-Dimethylaminophenyl)-1-phenyl-1H-pyrazole-3-amine;
N-(4-Methylphenyl)-1-phenyl-1H-pyrazol-3-amine;
N-(4-Chlorophenyl)-1-phenyl-1H-pyrazol-3-amine;
N-(3,4-Dimethoxyphenyl)-1-phenyl-1H-pyrazol-3-amine;
N-(4-Methylthiophenyl)-1-phenyl-1H-pyrazol-3-amine;
5-(4-Dimethylaminophenyl)-N-(4-methoxyphenyl)-1-phenyl-1H-pyrazol-3-amine;
N-(4-Methoxyphenyl)-1-[4-(phenylmethoxy)phenyl]-1H-pyrazol-3-amine;
4-(1-Phenyl-1H-pyrazol-3-yl)aminobenzonitrile;
N-(4-Methoxyphenyl)-1-(3-trifluoromethylphenyl)-1H-pyrazol-3-amine;
1-(4-Fluorophenyl)-N-(4-methoxyphenyl)-1H-pyrazol-3-amine;
N-(4-Phenoxyphenyl)-1-phenyl-1H-pyrazol-3-amine;
N-(4-Phenylaminophenyl)-1-phenyl-1H-pyrazol-3-amine;
N-(4-Methoxyphenyl)-1-phenyl-5-(2-phenylethyl)-1H-pyrazol-3-amine;
N-(3-Hydroxy-4-propylphenyl)-1-phenyl-1H-pyrazol-3-amine;
N-(4-Methoxyphenyl)-1-(2-naphthalenyl)-1H-pyrazol-3-amine;
4-[3-(4-Methoxyphenylamino)-1H-pyrazol-1-yl]-6-methylpyrimidine;
N-Benzyl-1-(3-trifluoromethylphenyl)-1-H-pyrazole-3-amine;
N-(4-Decyloxyphenyl)-1-phenyl-1H-pyrazol-3-amine;
4-(1-Phenyl-1H-pyrazol-3-yl)aminophenol;
4-[3-(4-Methoxyphenylamino)-1H-pyrazol-1-yl]phenol;
N-[4-(2-Diethylaminoethoxy)phenyl]-1-phenyl-1-H-pyrazol-3-amine;

Ethyl 4-[3-(4-methoxyphenylamino)-1H-pyrazol-1-yl]-phenoxyacetate;
Ethyl 4-[1-phenyl-1H-pyrazol-3-yl]aminophenoxy acetate;
1-[4-(2-Diethylaminoethoxy)phenyl]-N-(4-methoxyphenyl]-1H-pyrazol-3-amine;
4-[3-(4-Methoxyphenylamino)1H-pyrazol-1-yl]phenoxyacetic acid;
4-(1-[4-Methylphenyl]-1H-pyrazol-3-yl)aminophenylacetic acid;
4(1-Phenyl-1H-pyrazol-3-yl)aminophenylacetic acid;
4-[1-Phenyl-1H-pyrazol-3-yl]aminophenoxyacetic acid;
N-[(4-Diethylaminomethyl)phenyl]-1-phenyl-1H-pyrazol-3-amine;
N-(3-Acetyl-4-hydroxyphenyl)-1-phenyl-1H-pyrazol-3-amine;
N-(4-Methylsulphonylphenyl)-1-phenyl-1H-pyrazol-3-amine;
N-(4-Methylsulphinylphenyl)-1-phenyl-1H-pyrazol-3-amine;
5-Chloro-N-(4-methoxyphenyl)-1-phenyl-1H-pyrazol-3-amine; or
Methyl 4-(1-phenyl-1H-pyrazol-3-yl)aminobenzoate.

5. A method of treatment of an inflammatory condition, which comprises administration to a patient suffering from such a condition of an effective amount of a compound having the formula I

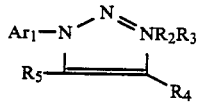

in which
$R_2$ represents $Ar_2$;
$R_3$ represents hydrogen, alkyl $C_1$ to $C_{18}$ or alkyl $C_1$ to $C_{18}$ substituted by $Ar_3$;
$R_4$ and $R_5$, which may be the same or different, each independently represent hydrogen, halogen, Ar, alkyl $C_1$ to $C_{18}$ or alkyl $C_1$ to $C_{18}$ substituted by Ar,
$Ar_1$, $Ar_2$ and Ar, which may be the same or different, each independently represent phenyl, naphthyl or either thereof substituted by one or more of halogen, hydroxy, —CN, —$COR_6$, trihalomethyl, alkoxy, alkoxy substituted by —$COR_6$, alkoxy substituted by —$NR_7R_8$, alkyl $C_1$ to $C_{18}$, alkyl $C_1$ to $C_{18}$ substituted by —$COR_6$, alkyl $C_1$ to $C_{18}$ substituted by $NR_7R_8$, alkoxy substituted by $Ar_3$, $S(O)_nR_9$, —$NR_7R_8$ or $OAr_3$;
$R_6$ represents —$OR_{10}$, —$NR_7R_8$ hydrogen alkyl $C_1$ to $C_{18}$;
$R_7$ and $R_8$, which may be the same or different, each independently represent hydrogen, alkyl $C_1$ to $C_{18}$, alkanoyl $C_1$ to $C_{18}$ or $Ar_3$;
$R_9$ represents alkyl $C_1$ to $C_{18}$ or $Ar_3$;
$R_{10}$ represents hydrogen, alkyl $C_1$ to $C_{18}$ or $Ar_3$;
m represents an integer from 3 to 6 inclusive; and
n represents 0, 1 or 2.

* * * * *